United States Patent
Ko et al.

(10) Patent No.: US 8,710,276 B2
(45) Date of Patent: Apr. 29, 2014

(54) CATALYST COMPOSITIONS FOR HYDROFORMYLATION REACTION AND HYDROFORMYLATION PROCESS USING THE SAME

(71) Applicant: LG Chem, Ltd., Seoul (KR)

(72) Inventors: Dong Hyun Ko, Daejeon (KR); Sung Shik Eom, Daejeon (KR); O Hak Kwon, Daejeon (KR); Hye Won Yang, Seoul (KR); Jae Hui Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/949,800

(22) Filed: Jul. 24, 2013

(65) Prior Publication Data

US 2013/0317256 A1    Nov. 28, 2013

Related U.S. Application Data

(63) Continuation of application No. PCT/KR2012/007465, filed on Sep. 18, 2012.

(30) Foreign Application Priority Data

May 24, 2012  (KR) ......................... 10-2012-0055114

(51) Int. Cl.
*C07C 45/50* (2006.01)
*B01J 31/12* (2006.01)
*B01J 31/24* (2006.01)

(52) U.S. Cl.
USPC ............ 568/454; 502/161; 502/162; 502/166

(58) Field of Classification Search
CPC .. C07C 45/50; C07C 45/505; B01J 2231/321; B01J 2531/822
USPC ................... 568/454; 502/165, 167, 161, 162
See application file for complete search history.

(56) References Cited

U.S. PATENT DOCUMENTS

| 4,201,728 A | * | 5/1980 | Hughes | ......................... 568/454 |
| 4,283,562 A | * | 8/1981 | Billig et al. | ................... 568/454 |
| 5,233,093 A | | 8/1993 | Pitchai et al. | |

FOREIGN PATENT DOCUMENTS

| KR | 0547587 B1 | 1/2006 |
| KR | 10-2009-0092281 A | 8/2009 |
| KR | 0964099 B1 | 6/2010 |
| KR | 10-1089488 B1 | 12/2011 |

* cited by examiner

*Primary Examiner* — Sikarl Witherspoon
(74) *Attorney, Agent, or Firm* — McKenna Long & Aldridge, LLP

(57) ABSTRACT

Disclosed are a catalyst composition for hydroformylation of olefin compounds, comprising a specific phosphine ligand and a transition metal catalyst, and a hydroformylation process using the same. Through a hydroformylation process using the catalyst composition according to the present invention, a suitable selectivity of iso-aldehyde can be maintained, catalyst stability can be improved, the amount of used ligand can be reduced and superior catalyst activity can be obtained.

10 Claims, No Drawings

CATALYST COMPOSITIONS FOR HYDROFORMYLATION REACTION AND HYDROFORMYLATION PROCESS USING THE SAME

This application is a Continuation Bypass of International Application No. PCT/KR2012/007465, filed on Sep. 18, 2012, which claims priority to Korean Patent Application No. 10-2012-0055114, filed on May 24, 2012, with the Korean Patent Office, both of which are incorporated herein in their entirety by reference.

BACKGROUND OF THE INVENTION

1. Field of the Invention

The present invention relates to a catalyst composition for hydroformylation and a hydroformylation process using the same. More specifically, the present invention relates to a catalyst composition for hydroformylation of olefin compounds, comprising a specific phosphine ligand and a transition metal catalyst, and a hydroformylation process using the same.

2. Description of the Related Art

A hydroformylation reaction, wherein linear (normal) and branched (iso) aldehydes, in which the number of carbon atoms is increased by one, are prepared by reacting various olefins with carbon monoxide (CO) and hydrogen ($H_2$), commonly called "synthetic gas", in the presence of a homogeneous organometallic catalyst and ligand was first found by Otto Roelen in 1938 in Germany.

Generally, the hydroformylation reaction known as an oxo reaction is an industrially important reaction in the homogeneous catalyst reaction and various aldehydes including about 9.60 million tons of alcohol derivatives are produced and used all over the world through an oxo process (SRI report, November 2002, 682. 7000A) in 2001.

Various aldehydes synthesized through the oxo reaction undergo condensation such as aldol condensation, and then are converted into acids and alcohols containing longer alkyl groups through an oxidation or hydrogenation process. In addition, after condensation reaction of aldol or the like, aldehydes may be oxidized or hydrogenated and then converted into various acids and alcohols containing a long alkyl group. In particular, the hydrogenated alcohol obtained by this oxo reaction is referred to as an oxo alcohol. The oxo alcohol is widely industrially used for solvents, additives, materials of various plasticizers and synthetic lubricants.

A metal-carbonyl compound catalyst is known to be active as a hydroformylation catalyst and the industrially used catalyst is generally based on cobalt (Co) and rhodium (Rh). N/I selectivity {ratio of linear (normal) to branched (iso) aldehyde}, activity and stability of produced aldehyde depend on the kind of catalysts and ligands and operation conditions.

At present, 70% or more of oxo plants in the world utilize a low pressure oxo process in which an excess phosphine ligand is applied to a rhodium-based catalyst due to high catalyst activity, high N/I selectivity and relatively easy reaction conditions in spite of problems such as high catalyst cost and deterioration in catalyst activity caused by poisoning.

As a central metal of a catalyst for oxo reaction, a transition metal such as cobalt (Co) and rhodium (Rh) as well as iridium (Ir), ruthenium (Ru), osmium (Os), platinum (Pt), palladium (Pd), iron (Fe), and nickel (Ni) may be used. The respective metals exhibit catalyst activity in the order of Rh>>Co>Ir, Ru>Os>Pt>Pd>Fe>Ni. Co, Rh, Pt and Ru are Group VIII transition metals, which exhibit superior catalyst activity during an oxo reaction. Pt and Ru are utilized only in research applications, most oxo processes for commercial applications are based on rhodium and cobalt, and representative examples thereof include $HCo(CO)_4$, $HCo(CO)_3PBu_3$ and $HRh(CO)(PR_3)_3$.

Ligands used for oxo processes include phosphine ($PR_3$, in which R represents $C_6H_5$ or $n-C_4H_9$), phosphine oxide ($O=P(C_6H_5)_3$) and phosphite. When rhodium is used as a central metal, a ligand that exhibits superior catalyst activity and stability, as compared to triphenylphosphine (TPP) is known to be almost not present. Accordingly, generally, a rhodium (Rh) metal is used as a catalyst for oxo processes, TPP is used as a ligand, and TPP as the ligand is used at an amount of 100 equivalents or more of the catalyst in order to improve catalyst stability.

Since among aldehydes, products of oxo reactions, linear aldehyde derivatives are generally valuable, most catalyst research has been focused on increase in ratio of linear aldehydes.

However, there is also increasing demand for techniques that can improve catalyst stability and reduce an amount of used ligand, while maintaining a suitable selectivity of iso-aldehyde.

SUMMARY OF THE INVENTION

As a result of repeated research to solve these problems, the present inventors discovered that selectivity of iso-aldehyde can be maintained at an optimal level, catalyst stability can be increased and the amount of used ligand can be reduced by applying a specific phosphine ligand to hydroformylation of olefins. The present invention was completed, based on this discovery.

That is, it is an object of the present invention to provide to provide a catalyst composition comprising a monodentate phosphine ligand and a transition metal catalyst that can improve catalyst stability, reduce an amount of used ligand and exert superior catalyst activity, and a hydroformylation process using the same.

In accordance with one aspect of the present invention, provided is a catalyst composition for hydroformylation comprising a monodentate phosphine ligand and a transition metal catalyst, wherein the monodentate phosphine ligand is at least one selected from cyclohexyldiphenylphosphine, cyclohexylditolylphosphine and cycloheptyldiphenylphosphine.

In accordance with another aspect of the present invention, provided is a process for hydroformylating an olefin compound, comprising reacting the olefin compound with a synthetic gas ($CO/H_2$) in the presence of the above_catalyst composition to obtain aldehyde having a normal/iso selectivity of 1.7 to 2.1.

DETAILED DESCRIPTION OF THE INVENTION

Hereinafter, the present invention will be described in more detailed.

The catalyst composition for hydroformylation reactions according to the present invention comprises a monodentate phosphine ligand and a transition metal catalyst, thereby improving catalyst stability and reducing an amount of used ligand during hydroformylation of olefins.

Hereinafter, respective ingredients of the catalyst composition of the present invention for hydroformylation reactions will be described in detail.

(a) Monodentate Phosphine Ligand

The catalyst composition for hydroformylation reactions of the present invention comprises a specific monodentate phosphine ligand. Since specific monodentate phosphine ligands used in the present invention are continuously consumed in the aldehyde recovery process during continuous hydroformylation, suitably selected ligands can be added into the reactor, thus being advantageously easily applicable to actual processes. The present invention developed a catalyst system that improves catalyst stability and reduces an amount of used ligand, while maintaining suitable selectivity of iso-aldehyde using only monodentate phosphine ligands.

More specifically, examples of the monodentate phosphine ligand include cyclohexyldiphenylphosphine (CHDP), cyclohexylditolylphosphine (CHDTP), cycloheptyldiphenylphosphine (CHpDP) and the like. The monodentate phosphine ligand may be used alone or in combination thereof in the present invention.

The content of the monodentate phosphine ligand is 5 to 100 moles, more preferably 10 to 50 moles, with respect to one mole of the central metal of the transition metal catalyst. When the content is lower than 5 moles, suitable ligands are insufficient and reactivity of catalysts may be not exhibited, and when the content exceeds 100 moles, reaction speed is disadvantageous due to presence of excess ligand.

In particular, when the catalyst composition comprises the cyclohexyldiphenylphosphine, cyclohexyldiphenylphosphine is most preferably present in an amount of 1.6 to 3.0% by weight, when the catalyst composition comprises cyclohexylditolylphosphine, the cyclohexylditolylphosphine is most preferably present in an amount of 1.5 to 1.8% by weight, and when the catalyst composition comprises cycloheptyldiphenylphosphine, the cycloheptyldiphenylphosphine is most preferably present in an amount of 1.2 to 1.5% by weight in terms of maximization of stability and activity of the catalyst and selectivity of iso-aldehyde.

The total content of the monodentate phosphine ligand is preferably 1.2 to 3.0% by weight with respect to the total weight of the catalyst composition. At this time, when the content of the ligand is lower than 1.2% by weight, a problem associated with catalyst stability occurs, and when the content exceeds 3.0% by weight, excess expensive ligand is inevitably used without obtaining specific effects, thus disadvantageously entailing an increase in cost.

(b) Transition Metal Catalyst

Examples of the transition metal catalyst of the catalyst composition for hydroformylation reactions according to the present invention include cobaltcarbonyl [$Co_2(CO)_8$], acetylacetonatodicarbonylrhodium [Rh(AcAc)(CO)$_2$], acetylacetonatocarbonyltriphenylphosphinerhodium [Rh(AcAc)(CO)(TPP), ROPAC], hydridocarbonyltri(triphenylphosphine)rhodium [HRh(CO)(TPP)$_3$], acetylacetonatodicarbonylirridium [Ir(AcAc)(CO)$_2$] or hydridocarbonyltri(triphenylphosphine)iridium [HIr(CO)(TPP)$_3$] and the like. The transition metal catalyst may be used alone or in combination thereof in the present invention. Preferably acetylacetonatodicarbonylrhodium [Rh(AcAc)(CO)$_2$] or acetylacetonatocarbonyltriphenylphosphinerhodium [Rh(AcAc)(CO)(TPP), ROPAC] is used alone or in combination thereof.

The content of central metal of the transition metal catalyst is preferably 10 to 1000 ppm, more preferably 50 to 500 ppm, based on the weight or volume of the catalyst composition. When the content of the central metal is lower than 10 ppm, hydroformylation reaction speed is decreased, thus being industrially disadvantageous, and when the content exceeds 500 ppm, cost is increased due to expensive central metal and reaction speed is not superior.

The present invention is also directed to a method for hydroformylating an olefin compound, comprising reacting an olefin compound with synthetic gases (CO/$H_2$) in the presence of the catalyst composition according to the present invention to obtain an aldehyde.

Specific ingredients and contents of the catalyst composition according to the present invention are described above. The catalyst composition of the present invention may be prepared by dissolving the ingredients in a solvent. For example, the solvent that can be used in the present invention is preferably at least one selected from, but is not limited to, aldehydes including propane aldehyde, butyl aldehyde, pentyl aldehyde, valeraldehyde and the like; ketones including acetone, methyl ethyl ketone, methyl isobutyl ketone, acetophenone, cyclohexanone and the like; alcohols including ethanol, pentanol, octanol, hexanol and the like; aromatics including benzene, toluene, xylene and the like; halogenated aromatics including orthodichlorobenzene; ethers including tetrahydrofuran, dimethoxyethane, dioxane and the like; halogenated paraffins including methylene chloride; and paraffin hydrocarbons including heptanes and the like, and is more preferably aldehyde produced by hydroformylation.

The olefin compound used for aldehyde preparation of the present invention comprises a compound represented by the following formula 1 below.

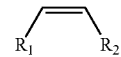

[Formula 1]

(wherein R1 and R2 each independently represent hydrogen, a $C_1$-$C_{20}$ alkyl group, fluorine (F), chlorine (Cl), bromine (Br), trifluoromethyl (—$CF_3$) or a $C_6$-$C_{20}$ aryl group having zero to 5 substituents, wherein the substituent of the aryl group is nitro (—$NO_2$), fluorine (F), chlorine (Cl), bromine (Br), methyl, ethyl, propyl or butyl).

Specifically, the olefin compound represented by Formula 1 is ethene, propene, 1-butene, 1-pentene, 1-hexene, 1-oxtene, styrene or the like and may be used alone or in combination thereof.

The synthetic gas used for the aldehyde preparation method according to the present invention is a mixture of carbon monoxide and hydrogen and a mix ratio of CO to $H_2$ is preferably 5:95 to 70:30, more preferably 40:60 to 60:40, most preferably 50:50 to 40:60, but is not limited thereto. When the mix ratio of synthetic gas (CO:$H_2$) is lower than 5:95 or is higher than 70:30, the gas not used for reaction is excessively accumulated in the reactor and catalyst reactivity may thus be decreased.

In the hydroformylation process of the olefin compound according to the present invention, reaction conditions other than the catalyst composition according to the present invention may be selected from general methods well-known in the art.

In the process of preparing aldehyde according to the present invention, a temperature at which an olefin compound reacts with a synthetic gas (CO/$H_2$) in the presence of the catalyst composition is preferably 20 to 180° C., more preferably 50 to 150° C., most preferably 75 to 125° C. When the reaction temperature is lower than 20° C., hydroformylation reaction disadvantageously does not occur and, when the reaction temperature exceeds 180° C., catalyst stability is greatly deteriorated and catalyst activity is disadvantageously decreased.

Also, the reaction pressure is preferably 1 to 700 bar, more preferably 1 to 300 bar, most preferably 5 to 30 bar. When the reaction pressure is lower than 1 bar, the hydroformylation reaction hardly occurs, and when the reaction pressure exceeds 700 bar, considerably expensive reactors should be used due to explosion risk without specific gain in activity, thus being industrially disadvantageous.

Specifically, the hydroformylation process of the olefin compound according to the present invention may be schematically depicted by the following equation 1.

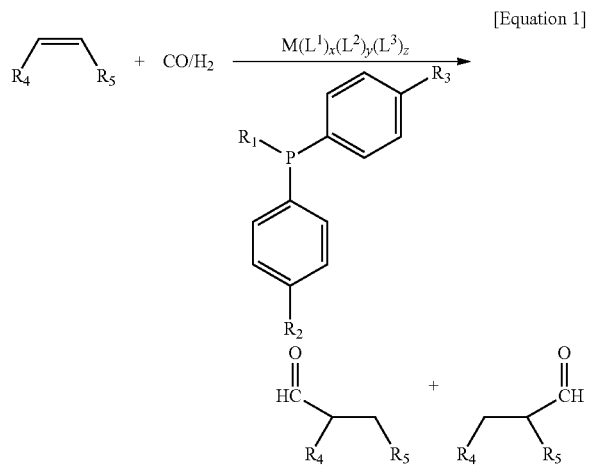

[Equation 1]

First, a transition metal catalyst 2 and a ligand 1 are dissolved in a solvent such as benzene, toluene, ethanol, pentanol, octanol, hexanol, butylaldehyde or pentylaldehyde to prepare a mix solution of the transition metal catalyst and the ligand. Then, the mix solution, an olefin compound 3, and a synthetic gas 4 of carbon monoxide and hydrogen are supplied to a reactor, followed by performing a hydroformylation reaction through heating and pressurizing with stirring, to prepare aldehyde.

As can be seen from the following examples, in spite of lower ligand content than conventional cases, the catalyst composition according to the present invention satisfies an aldehyde N/I selectivity of 1.7 to 2.1 and, at the same time, a catalyst stability of 55 to 64% after 15 hours, a catalyst stability of 63 to 73% after 5 hours, and a catalyst stability of 71 to 90% after 2.5 hours, with respect to a fresh catalyst activity of 108 to 130%. Hereinafter, the present invention will be described in more detailed with reference to the following examples. However, these examples are provided only for illustration and should not be construed as limiting the technical scope of the present invention.

CONTROL EXAMPLE

Hydroformylation of Propene Using acetylacetonatocarbonyltriphenylphosphinerhodium (Rh(AcAc)(CO)(TPP)

0.0957 g (0.194 mmol) of ROPAC (rhodium acetylacetonato carbonyl triphenylphosphine (Rh(acac)(CO)PPh$_3$) as a catalyst was dissolved in butylaldehyde as a solvent such that the weight of the resulting solution reached 100 g and the solution was added to a 600 ml auto-clave reactor. Propene, CO and H$_2$ were added to the reaction solution and these ingredients were reacted at a reactor inner pressure of 8 bar and at 90° C. for one hour.

The activity (%) of fresh catalyst used for the reaction and normal/iso selectivity of prepared aldehyde were measured, catalyst stability was measured for 15 hours or less through stability testing and the results thus obtained are summarized in Tables 1 and 2.

At this time, catalyst activity (%) was obtained by dividing the total amount of aldehyde prepared during the reaction into molecular weight of butylaldehyde, concentration of used catalyst or reaction time, and the unit was mol(BAL)/mol(Rh)/h. The normal/iso selectivity of prepared aldehyde was obtained by dividing the amount of normal-butylaldehyde prepared during reaction into the amount of iso-butylaldehyde, and the amount of each prepared aldehyde was measured by gas chromatography (GC) analysis.

Stability test (aging test) was carried out by adding a gas containing CO and H$_2$ having a molar ratio of 1:1 to the solution, maintaining an inner pressure of the reactor at 10 bar, performing an aging test at 120° C. while stirring, and observing variation with time.

Examples 1-5

A test was performed in the same manner as in Control Example except that 3% by weight 2.8% by weight, 2.4% by weight, 2.0% by weight and 1.6% by weight of cyclohexyldiphenylphosphine (CHDP) were sequentially used, instead of 6% by weight of TPP. The results thus obtained are shown in Tables 1 and 2.

Examples 6-7

A test was performed in the same manner as in Control Example except that 1.8% by weight and 1.5% by weight of cyclohexylditolylphosphine (CHDTP) were sequentially used, instead of 6% by weight of TPP. The results thus obtained are shown in Tables 1 and 2.

Examples 8-9

A test was performed in the same manner as in Control Example except that 1.5% by weight and 1.2% by weight of cycloheptyldiphenylphosphine (CHpDP) were sequentially used, instead of 6% by weight of TPP. The results thus obtained are shown in Tables 1 and 2.

Comparative Example 1

A test was performed in the same manner as in Control Example except that 3% by weight of TPP was used, instead of 6% by weight of TPP. The results thus obtained are shown in Tables 1 and 2.

TABLE 1

| No. of Example | Catalyst solution | Fresh catalyst activity % | Normal/iso ratio |
|---|---|---|---|
| Control Ex. | TPP 6.0 wt % | 100 | 9.5 |
| Ex. 1 | CHDP 3.0 wt % | 105 | 2.1 |
| Ex. 2 | CHDP 2.8 wt % | 109 | 2.1 |
| Ex. 3 | CHDP 2.4 wt % | 118 | 2.0 |
| Ex. 4 | CHDP 2.0 wt % | 130 | 2.0 |
| Ex. 5 | CHDP 1.6 wt % | 145 | 1.9 |
| Ex. 6 | CHDTP 1.8 wt % | 108 | 1.8 |
| Ex. 7 | CHDTP 1.5 wt % | 115 | 1.7 |
| Ex. 8 | CHpDP 1.5 wt % | 105 | 1.9 |
| Ex. 9 | CHpDP 1.2 wt % | 113 | 1.8 |
| Comp. Ex. 1 | TPP 3.0 wt % | 142 | 8.3 |

TABLE 2

| No. of Example | Catalyst solution | Catalyst stability test (aging time) | | | |
|---|---|---|---|---|---|
| | | Fresh | 2.5 hr | 5.0 hr | 15.0 hr |
| Control Ex. | TPP 6.0 wt % | 100 | 52 | 48 | 37 |
| Ex. 1 | CHDP 3.0 wt % | 105 | 71 | 64 | 56 |
| Ex. 2 | CHDP 2.8 wt % | 109 | 72 | 63 | 56 |
| Ex. 3 | CHDP 2.4 wt % | 118 | 76 | 65 | 58 |
| Ex. 4 | CHDP 2.0 wt % | 130 | 83 | 69 | 59 |
| Ex. 5 | CHDP 1.6 wt % | 145 | 90 | 70 | 57 |
| Ex. 6 | CHDTP 1.8 wt % | 108 | 77 | 69 | 62 |
| Ex. 7 | CHDTP 1.5 wt % | 115 | 82 | 73 | 64 |
| Ex. 8 | CHpDP 1.5 wt % | 105 | 69 | 61 | 54 |
| Ex. 9 | CHpDP 1.2 wt % | 113 | 73 | 62 | 51 |
| Comp. Ex. 1 | TPP 3.0 wt % | 142 | 52 | 44 | 26 |

As can be seen from Tables 1 and 2 above, when comparing Examples 1 to 9, Comparative Example 1, and Control Example, effects of specific monodentate phosphine ligand used for the present invention can be confirmed.

As apparent from the fore-going, the catalyst composition according to the present invention and a hydroformylation process using the same can improve catalyst stability, while maintaining a suitable selectivity of iso-aldehyde, thus maintaining catalyst activity and reducing an amount of used ligand by applying a specific phosphine ligand to hydroformylation reaction of olefins.

Also, since specific phosphine ligands used for the present invention are continuously consumed during the aldehyde recovery process of continuous hydroformylation process, selected ligands can be further added to the reactor and can thus be practically directly applied to oxo processes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A catalyst composition for hydroformylation comprising a monodentate phosphine ligand and a transition metal catalyst,
    wherein the monodentate phosphine ligand is at least one selected from cyclohexyldiphenylphosphine, cyclohexylditolylphosphine and cycloheptyldiphenylphosphine,
    wherein the content of the total monodentate phosphine ligand is 1.2 to 3.0% by weight with respect to the total weight of the catalyst composition, and
    wherein the catalyst composition has an aldehyde normal/iso selectivity of 1.7 to 2.1.

2. The catalyst composition according to claim 1, wherein the content of the monodentate phosphine ligand is 0.5 to 200 moles, with respect to one mole of the central metal of the transition metal catalyst,
    wherein the transition metal catalyst is at least one selected from the group consisting of cobaltcarbonyl [Co$_2$(CO)$_8$], acetylacetonatodicarbonylrhodium [Rh(AcAc)(CO)$_2$], acetylacetonatocarbonyltriphenylphosphinerhodium [Rh(AcAc)(CO)(TPP)], hydridocarbonyltri(triphenylphosphine)rhodium [HRh(CO)(TPP)$_3$], acetylacetonatodicarbonylirridium [Ir(AcAc)(CO)$_2$] and hydridocarbonyltri(triphenylphosphine)iridium [HIr(CO)(TPP)$_3$].

3. The catalyst composition according to claim 1, wherein the catalyst composition comprises 1.6 to 3.0% by weight of cyclohexyldiphenylphosphine as the monodentate phosphine ligand, with respect to the total weight of the catalyst composition.

4. The catalyst composition according to claim 1, wherein the catalyst composition comprises 1.5 to 1.8% by weight of cyclohexyldiphenylphosphine as the monodentate phosphine ligand, with respect to the total weight of the catalyst composition.

5. The catalyst composition according to claim 1, wherein the catalyst composition comprises 1.2 to 1.5% by weight of cycloheptyldiphenylphosphine as the monodentate phosphine ligand, with respect to the total weight of the catalyst composition.

6. The catalyst composition according to claim 1, wherein the catalyst composition is dissolved in a solvent and is then applied to the hydroformylation reaction, wherein the solvent is at least one selected from the group consisting of propane aldehyde, butyl aldehyde, pentyl aldehyde, valeraldehyde, acetone, methyl ethyl ketone, methyl isobutyl ketone, acetophenone, cyclohexanone, ethanol, pentanol, octanol, hexanol, benzene, toluene, xylene, orthodichlorobenzene, tetrahydrofuran, dimethoxyethane, dioxane, methylene chloride and heptane.

7. A process for hydroformylating an olefin compound, comprising reacting the olefin compound with a synthetic gas (CO/H$_2$) in the presence of the catalyst composition according to claim 1 to obtain aldehyde having a normal/iso selectivity of 1.7 to 2.1.

8. The process according to claim 7, wherein the olefin compound comprises a compound represented by the following Formula 1:

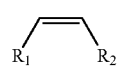

[Formula 1]

(wherein R1 and R2 each independently represent hydrogen, a C$_1$-C$_{20}$ alkyl group, fluorine (F), chlorine (Cl), bromine (Br), trifluoromethyl (—CF$_3$) or a C$_6$-C$_{20}$ aryl group having zero to 5 substituents, wherein the substituent of the aryl group is nitro (—NO$_2$), fluorine (F), chlorine (Cl), bromine (Br), methyl, ethyl, propyl or butyl).

9. The process according to claim 7, wherein a mix ratio of CO to H$_2$ constituting the synthetic gas is 5:95 to 70:30.

10. The process according to claim 7, wherein the catalyst composition is dissolved in a solvent and is then added to the reaction, wherein the solvent is at least one selected from the group consisting of propane aldehyde, butyl aldehyde, pentyl aldehyde, valeraldehyde, acetone, methyl ethyl ketone, methyl isobutyl ketone, acetophenone, cyclohexanone, ethanol, pentanol, octanol, hexanol, benzene, toluene, xylene, orthodichlorobenzene, tetrahydrofuran, dimethoxyethane, dioxane, methylene chloride and heptane.

* * * * *